United States Patent
Goeke et al.

(10) Patent No.: US 9,701,606 B2
(45) Date of Patent: Jul. 11, 2017

(54) PROCESS FOR THE PREPARATION OF METHOXYMELONAL

(71) Applicant: Givaudan S.A., Vernier (CH)

(72) Inventors: Andreas Goeke, Winterthur (CH); Yue Zou, Shanghai (CN)

(73) Assignee: Givaudan S.A., Vernier (CH)

( * ) Notice: Subject to any disclaimer, the term of this patent is extended or adjusted under 35 U.S.C. 154(b) by 124 days.

(21) Appl. No.: 14/350,508

(22) PCT Filed: Oct. 11, 2012

(86) PCT No.: PCT/EP2012/070109
§ 371 (c)(1),
(2) Date: Apr. 8, 2014

(87) PCT Pub. No.: WO2013/053787
PCT Pub. Date: Apr. 18, 2013

(65) Prior Publication Data
US 2014/0357547 A1    Dec. 4, 2014

(30) Foreign Application Priority Data

Oct. 11, 2011  (WO) ............... PCT/CN2011/080634

(51) Int. Cl.
C07C 45/40    (2006.01)
C11B 9/00    (2006.01)

(52) U.S. Cl.
CPC ............ *C07C 45/40* (2013.01); *C11B 9/0015* (2013.01); *C07C 2523/44* (2013.01)

(58) Field of Classification Search
CPC .................................................... C07C 45/40
See application file for complete search history.

(56) References Cited

U.S. PATENT DOCUMENTS

| 4,311,617 A  * | 1/1982 | Ansari ................... C07C 43/13 512/25 |
| 2007/0276165 A1* | 11/2007 | Gutsche ................. C07B 41/08 568/959 |

FOREIGN PATENT DOCUMENTS

| DE | 102009001569 A1 | 9/2010 |
| GB | 859568 A | 1/1961 |
| JP | S51-143607 A | 12/1976 |
| JP | 2008-501715 A | 1/2008 |
| WO | WO 2005/118565 A1 | 12/2008 |
| WO | WO 2009/027957 A2 | 3/2009 |

OTHER PUBLICATIONS

PCT/EP2012/070109, International Search Report, mailed Jan. 17, 2013.
PCT/EP2012/070109, International Written Opinion, mailed Jan. 17, 2013.
PCT/EP2012/070109, International Preliminary Report on Patentability, mailed Apr. 15, 2014.
Japanese Office Action mailed Jun. 23, 2016 for corresponding Japanese Patent Application No. 2014-535063.
Author Unknown, "The forth series of experimental chemistry 23: Organic synthesis V; Oxidation Reaction", The Chemical Society of Japan, Oct. 7, 1991, vol. 23, pp. 457-459.
Gallagher, et al., "Stille Reactions Catalytic in Tin: A "Sn—F" Route for Intermolecular and Intramolecular Couplings", J. Org. Chem. 2005, 70(3), pp. 841-846.
Kobori, et al., "Substrate Specificity and Carbohydrate Synthesis Using Transketolase", J. Org. Chem. 1992, vol. 57, No. 22, pp. 5899-4907.
Suhara, et al., "Synthesis and biological evaluation of several structural analogs of 2-arachidonoylglycerol, an endogenous cannabinoid receptor ligand", Bioorg. Med. Chem. 2007, vol. 15, No. 2, pp. 854-867.

* cited by examiner

*Primary Examiner* — Lanee Reuther
(74) *Attorney, Agent, or Firm* — Curatolo Sidoti Co., LPA; Joseph G. Curatolo; Salvatore A. Sidoti

(57) ABSTRACT

A process of forming methoxymelonal comprising the steps of treating a solution of citronellene to ozonolysis, and hydrogenating the product formed to provide methoxymelonal.

4 Claims, No Drawings

PROCESS FOR THE PREPARATION OF METHOXYMELONAL

CROSS REFERENCE TO RELATED APPLICATIONS

This application is a national stage application of International Application No. PCT/EP2012/070109, filed 11 Oct. 2012, which claims priority from International Patent Application No. PCT/CN2011/080634, filed on 11 Oct. 2011, from which applications priority is claimed, and which are incorporated herein by reference.

This invention relates to the compound 6-methoxy 2,6-dimethylheptanal (methoxymelonal), a method of forming the compound and compositions containing said compound.

Methoxymelonal is a known perfume ingredient. It is a classical perfume ingredient with a powerful fruity, floral and green note. It is currently prepared by a 4-step synthesis that is described in German patent application DE2624104 filed in 1976. The synthesis proceeds by the epoxidation of methoxycitronellene, followed by alkaline hydrolysis of the epoxide to form a diol, which is in turn is oxidised to a ketoalcohol. Finally the ketoalcohol is cleaved to yield methoxymelonal.

This synthetic pathway is somewhat complicated and the compound is consequently expensive to prepare. As a result, despite its attractive odour characteristics, methoxymelonal currently is used in low volumes and in high end products such as fine perfumery.

There remains a need to provide a process of producing methoxymelonal in a relatively low cost manner.

The invention provides in a first aspect a process of forming methoxymelonal comprising the steps of subjecting citronellene (2) to ozonolysis, followed by a reductive work-up to give methoxymelonal. The synthesis is set out in the scheme below:

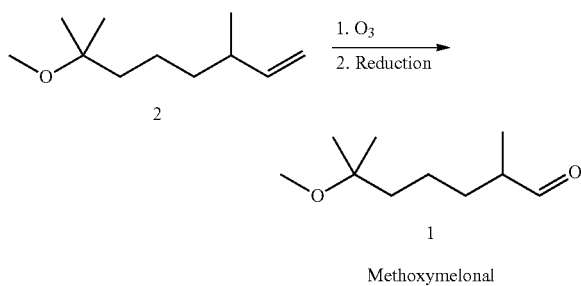

Methoxymelonal

Ozonolysis reactions are well known in the art of synthetic organic chemistry and are described in detail in text books. As such, there is no need to go into great detail here. In a specific embodiment, however, ozonolysis is carried out by bubbling ozone through a solution of the starting material (2) in a suitable solvent, for example a lower alcohol, e.g. methanol, or water at a temperature range of about −70 to +50 degrees centigrade, more particularly about 0 degrees to +30 degrees centigrade.

Reductive work-up, e.g. hydrogenation, is likewise well known in the art of synthetic organic chemistry and there is no need to enter into great detail here. In a specific embodiment, however, to the reaction product from the ozonolysis step is added a reducing agent, e.g. palladium supported on carbon under an atmosphere of hydrogen. Hydrogenation may proceed at a temperature range of about −40 to +30, more particularly about −20 degrees centigrade.

In another particular embodiment, the reductive work-up can be performed in aqueous. sulfite solutions, as set forth in more detail in example 2, below.

Methoxymelonal thus formed can be purified using standard purification techniques well known in the art, for example chromatographic techniques, such as silica gel chromatography.

The starting material (2) is citronellene and is a readily available starting material. Citronellene synthesis is described in the literature, see for example GB 859568.

As stated hereinabove, methoxymelonal is a well known perfumery ingredient and it can be compounded according to known techniques with other perfumery ingredients to form fragrance compositions. Said other perfumery ingredients are well known in the art and many are described in "Perfume and Flavour Chemicals", S. Arctander, Allured Publishing Corporation, 1994, IL, USA, which is incorporated herein by reference.

In particular, methoxymelonal is a fragrance that is somewhat similar in character and odour profile as p.tert-butyl-alpha-methyldihydrocinnamic aldehyde, which is also known as Lilial®. This is a discovery of some interest to perfumers as the use of Lilial has recently come under scrutiny pursuant to reports that it might have mutagenic properties. Lilial is an extremely important molecule in the fragrance industry as it is used in very high volumes in all manner of consumer product applications. It would be highly desirable to find a perfume ingredient that was able to substantially replace Lilial in perfumery for use in consumer product applications, such that perfume compositions could be created having a lilial-like odour that contain reduced levels of lilial, or even no lilial.

Accordingly, in another aspect of the present invention there is provided a method of producing a lilial-like odour in a composition comprising the step of adding to said composition methoxymelonal formed according to a process herein described.

In yet another aspect of the invention there is provided a composition having a lilial-like odour comprising methoxymelonal formed according to a process herein described.

Of course, methoxymelonal does not have an odour profile that corresponds precisely to that of Lilial. As such, in a particular embodiment of the present invention methoxlmelonal is formulated with one or more additional fragrance ingredients that together provide a fragrance impression that is substantially equivalent to Lilial.

By "substantially equivalent" is meant that a panel of non-experts, e.g. a consumers would be unable to detect a difference between a consumer product, e.g. a detergent, containing lilial and the same product containing the replacement fragrance.

In a particular embodiment of the present invention methoxymelonal prepared according to the method described herein may be mixed with one or more ingredients selected from the group consisting of: 3-(4-tert-Butylphenyl)propionaldehyde (Bourgeonal), 2-Methyl-4-phenylbutan-2-ol (Dimethylphenylethylcarbinol), cis-4-(Isopropyl)cyclohexanemethanol (Mayol), 1-(1-hydroxyethyl)-4-(1-methylethyl)cyclohexane (Mugetanol), (4-Methyl-3-pentenyl)cyclohexenecarbaldehyde (Citrusal), 3-(p-(2-Methylpropyl)phenyl)-2-methylpropionaldehyde (Silvial), 3-p-Cumenyl-2-methylpropionaldehyde (Cyclamenaldehyde), mixture of: cis-tetrahydro-2-isobutyl-4-methylpyran-4-ol; trans-tetrahydro-2-isobutyl-4-methylpyran-4-ol (Florol), 5,9-Dimethyl-4,8-decadienal (Geraldehyde), beta.-methyl-3-(1-methylethyl)benzenepropanal (Florhydral), Octahydro-8,8-dimethylnaphthalene-2-carbaldehyde (Cyclomyral), alpha.-Methyl-1,3-benzodioxole-5-propionaldehyde (Helional), 5-Methyl-2-(1-methylbutul)-5-propyl-1,3-dioxan (Troenan), 3-(o-Ethylphenyl)-2,2-dimethylpropionaldehyde (Floralozone), Farnesol, 3,7,11-Trimethyldodeca-1,6,10-trien-3-ol, (mixture of isomers) (Nerolidol), Cyclohexylsalicylate, Hexylsalicylate, Benzylsalicylate, Amylsalicylate, Triethylcitrate, Dipropylenglycol, n-Pentyl salicylate; Methyl-N-(7-hydroxy-3,7-dimethyloctylidene)anthranilate; Benzoic acid, 2-hydroxy-, phenylmethyl ester; 4-(1,1-Dimethylethyl)benzenepropanal; Benzoic acid, 2-hydroxy-, 3-hexenyl ester, (Z)-; Acetaldehyde, [(3,7-dimethyl-6-octenyl)oxyl-; Propanal, 3-(4-isopropylphenyl)-; Benzoic acid, 2-hydroxy-, cyclohexyl ester; Octahydro-8,8-dimethylnaphthalene-2-carboxaldehyde; dl-3,7-Dimethyl-6-octen-1-ol; trans-3,7-Dimethyl-2,6-octadien-1-ol; Cyclopentan-1-ol, 2 Pentyl; Benzenepropanal, .alpha.-methyl-4-(1-methylethyl)-; Octahydro-4,7-methanoindanilydenebutanal; 1,6-Nonadien-3-ol, 3,7-dimethyl-; 4,8-Dimethyldeca-4,9-dienal; Benzenepropanal, .beta.-methyl-3-(1-methylethyl)-; 2-(2-Methylpropyl)-4-methyl-tetrahydro-2H-pyran-4-ol; 2-Butyl-4,6-dimethyldihydropyran (isomers); Benzoic acid, 2-hydroxy-, hexyl ester; 2-Methyl-3-(3,4-methylenedioxyphenyl)-propanal; Octanal, 7-hydroxy-3,7-dimethyl-; 1,6-Octadien-3-ol, 3,7-dimethyl-; 3-Cyclohexene-1-carboxaldehyde, 4-(4-hydroxy-4-methyl-pentyl)-; 2,2-Dimethyl-3-(3-methylphenyl)-propanol; Cyclohexanemethanol, 4-(1-methylethyl)-, cis-; 2-Naphthaldehyde, 1,2,3,4,5,6,7,8-octahydro-8,8-dimethyl-(mixture); 2,6-Dimethyl-5-heptenal; 1-(4-Isopropylcyclohexyl)ethanol; 3-methyl-4-phenylbutan-2-ol; Dimethyl phenyl Propanol; 1H-Indene-ar-propanal. 2,3-dihydro-1,1-dimethyl-; Lilial/methyl anthranilate Schiff base; 2-Cyclohexylidene-2-phenylacetonitrile; 3-Methyl-5-phenyl-1-pentanol; 1-methyl-3-(2-methylpropyl)cyclohexan-1-ol; 2-Methyl-3-(4-(2-methylpropyl)phenyl)propanal; 3-(4-Isobutyl-phenyl)-2-methyl-propionaldehyde; 2-Octanol, 2,6-dimethyl-; 3,7-Dimethyloctanol-3; 2-[(4-methylphenyl)methylenel-heptanal; Methyl 2-hexyl-3-oxo-cyclopentanecarboxylate; alpha-Hexylcinnamaldehyde; Cyclopentaneacetic acid, 2-oxo-2 Phenyl-, methyl ester; (3-hydroxy-2-butanone); 2,6,10-Trimethyl-9-undecenal; 2-H 1,5-Benzodioxepin-3(4H)-one, 7 propyl-; 4H-4A, 9 Methanoazuleno (5,6 d)-1,3-dioxole, octahydro 2,2,5,8,8,9a-hexamethyl-; 3a,6,6,9a-Tetramethyl-dodecahydronaphtho[2,1-b]furan; 7(3-methyl butyl)-1,5-Benzodioxepin-3-one; 2-Ethyl-4-(2,2,3-trimethylcyclopent-3-enyl-1)-2-buten-1-ol; 3,4-Dioxy(cycloacetonyl)toluene; 3a,6,6,9a-Tetramethyl-dodecahydronaphtho[2,1-b]furan; 2-Propenol-1,3-phenyl-; 3,7-Dimethyl-2,6-octadienal; Hexahydro-4,7-methanoinden5(6)yl isobutyrate; Hexahydro-4,7-methanoinden-5(6)-yl acetate; Hexahydro-4,7-methanoinden-5(6)-yl propionate; Cyclohexadecanolide; 8-Cyclohexadecen-1-one; Cyclopentadecanone; 4-(2,6,6-Trimethyl-3-cyclohexen-1-yl)-but-3-en-4-one; 3-Methyl-5-(2,2,3-trimethyl-3-cyclopenten-1-yl)-4-penten-2-ol (& isomers); 1,6-Octadiene, 3-(1-ethoxyethoxy)-3,7-dimethyl-; Benzaldehyde, 3-ethoxy-4-hydroxy-; 1,4-Dioxacycloheptadecane-5,17-dione; 4-Cyclopentadecen-1-one, (Z)-; Oxacyclohexadecan-2-one; alpha,alpha-Dimethyl-p-ethylphenylpropanal; 1,4, Cyclohexanedicarboxylic acid, diethyl ester; gamma-Decalactone; Oxacyclohexadecen-2-one; 1-Propanol, 2-[1-(3,3-dimethyl-cyclohexyl) ethoxyl-2-methyl-propanoate; 1,3,4,6,7,8-Hexahydro-4,6,6,7,8,8-hexamethyl-cyclopenta-(g)-2-benzopyran; Cyclododecaneethanol, .beta.-methyl-; 3-Acetyl-3,4,10,10-tetramethylbicyclo[4.4.01decane; Isohexenyl cyclohexenyl carboxaldehyde; 4-Acetoxy-3-pentyl-2H-tetrahydropyran and isomers; (1-Methyl-2-(1,2,2-trimethylbicyclo[3.1.01-hex-3-ylmethyl)cyclop-ropyl)methanol (Mixture of diastereoisomers); Dodecanal; gamma-Methyl benzenepentanal; 5-Cyclopentadecen-1-one, 3 Methyl; 7-Acetyl-1,1,3,4,4,6-hexamethyltetralin; 2-(2(4-Methyl-3-cyclohexen-1-yl)propyl)-cyclopentanone; 1-(2,2,6-Trimethylcyclohexyl)hexanol-3; 1-(1,1-dimethylpropyl)-4-ethoxycyclohexane (mixture of cis & trans isomers); 4-(4-Hydroxyphenyl) butanone-2; 2-Norpinene-2-Propionaldehyde,6,6-Dimethyl; Acetic Acid, (1-oxopropoxy)-1-(3,3-dimethylcyclohexyl) ethyl ester; 2-ethyl-4-(2,2,3-trimethyl-3-cyclopenten-1-yl)-2-buten-1-ol; Cyclohexadecanolide and Cyclopentadecanone mixture; Terpineol (alpha,beta,gamma); Benzaldehyde, 4-hydroxy-3-methoxy-; and 5-Cyclohexadecenone-1.

WO2009027957, which is hereby incorporated by reference, describes a series of mixtures of ingredients that may be employed in a perfume composition. In particular embodiments of the present invention the methoxymelonal of the present invention may be admixed with one or more of these ingredients, or with particular cocktails or mixtures described therein.

Methoxymelonal may be employed in compositions as hereinabove described in amounts ranging from 0.01 to 30% by weight of the perfume composition.

Any of the ingredients aforementioned that may be co-formulated with methoxymelonal to form a perfume composition may be employed in amounts ranging from 1 to 10% by weight of the perfume composition.

The lilial replacement composition need not be limited to a mixture of those ingredients mentioned above, and other ingredients commonly used in perfumery may be employed, for example any of those ingredients described in the Arctander reference described above, including essential oils, plant extracts, absolutes, resinoids, odourants obtained from natural products and the like.

Perfume compositions of the present invention may also contain commonly employed adjuvants such as solvents, e.g. ethanol or dipropylene glycol, emulsifiers and the like.

The lilial replacement composition uses a mixture of ingredients to reproduce the character of a single ingredient. These ingredients all have different properties, such as volatility and substantivity. Accordingly, for the replacement composition to retain a coherent character of lilial, it may be desirable to accelerate or retard the release of one or more ingredients depending on the particular end use. For example, when the perfume composition is to be used in a laundry detergent composition, it might be desirable to formulate one or more non-substantive ingredients in a delivery vehicle that provides the ingredient(s) with the requisite substantivity such that the character of lilial is evident on the laundered fabric.

Alternatively, in an end use application where a perfume is expected to bloom upon dilution, such as in the case of a hard-surface cleaner, it will be desirable to formulate the ingredients in such a manner that the individual ingredients develop at substantially the same rate during the cleaning period.

Accordingly, one or more of the ingredients employed in said perfume composition may be formulated in a delivery vehicle to provide a desired effect. Delivery vehicles may include encapsulates. Alternatively, the delivery vehicle may be in the form of a solid support, e.g. a polymeric support material onto which one or more perfume ingredients may be chemically or physically bound. Still further, one or more perfume ingredients may be dissolved or dispersed in a matrix material, which serves to control the rate at which said ingredient or ingredients emanates. In yet an alternative embodiment, one or more ingredients may be supported on a porous substrate, such as a cyclodextrin or a zeolite or other inorganic material. In a still further embodiment, one or more ingredients may be provided in the form of a pro-perfume, which will react in a suitable environment to release the perfume ingredient in a controlled manner.

Heretofore, the use of methoxymelonal has been somewhat limited to fine perfumery because of its prohibitive expense, however, the lower production costs associated with the process of the present invention means that it can have much wider application in all manner of household and personal care products.

A non-limiting list of applications include a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover.

Particular examples of cleaning products include the toilet cleaners or lavatory cleaners, these products being supplied in the form of powders, blocks, tablets or liquids, or gels, pipe-cleaning products or drain cleaners, universal or all-purpose or general-purpose cleaners, such as those used universally for all hard surfaces in the household and in commerce that can be wiped down wet or damp, sanitary cleaners, oven cleaners or grill cleaners which may be presented in the form of gels or foam sprays, metal polishes, including those supplied as polishing cloths, dipping baths, pastes, and liquids; glass cleaners and window cleaners; all special-purpose cleaning products, for example those for glass-ceramic hobs; carpet cleaners and stain removers.

Particular examples of autocare products include paint preservers, paint polishes, paint cleaners, wash preservers, shampoos for auto washing, auto-wash and wax products, polishes for trim metals, protective films for trim metals, plastics cleaners, tar removers, screen cleaners, engine cleaners and the like.

Particular examples of cosmetic products include cosmetic skincare products, e.g. bath products, skin washing and cleansing products, skincare products, eye makeup, lip care products, nail care products, intimate care products, foot care products; cosmetic products with specific effects, such as sunscreens, tanning products, de-pigmenting products, deodorants, antiperspirants, hair removers, shaving products; cosmetic dental-care products, such as dental and oral care products, toothcare products, cleaners for dental prostheses, adhesives for dental prostheses; cosmetic hair care products, e.g. hair shampoos, hair care products, hair setting products, hair-shaping products, and hair coloring products.

Particular examples of textile treatment products include detergents or fabric conditioners.

Particular examples of air fresheners and room fragrancers include fragrancers for spaces such as autos, cupboards, dishwashers, refrigerators or shoes, and vacuum cleaners.

EXAMPLE 1

In a 1500 ml flask, 90 g of methoxy citronellene 2 was dissolved in 900 ml of methanol. The mixture was cooled to −65° C. and ozone was bubbled through the mixture leading to an increased temperature of −55° C. After 1.5 h, the apparatus was evacuated in slight vacuum and flushed with nitrogen. This procedure was repeated a few times in order to make sure that ozone and oxygen were removed. Next, 5.0 g of palladium on carbon (10%) were added to the mixture at −20° C. and the nitrogen atmosphere was replaced by hydrogen. Under vigorous stirring, the hydrogenation proceeded while the temperature rose to +30° C. during 3 h. The internal temperature was then kept at 25° C. until no further hydrogen up-take was observed. The catalyst was filtered off, the filtrate was concentrated in vacuo and the residue was purified by chromatography on silica (hexane:MTBE 96:4) to yield 26 g (20%) of pure methoxymelonal (1).

1. $O_3$
2. $H_2$, Pd/C

2

1

Methoxymelonal

EXAMPLE 2

In a 250 ml flask, 8.5 g of methoxy citronellene 2 was suspended in 50 ml of water. The mixture was cooled to 0° C. by an ice-water bath. Under vigorous stirring, ozone was bubbled through the mixture leading to an increased temperature of 10° C. After 30 min, the ozonizer voltage was set to zero, and the reaction was flushed with oxygen for 5 min in order to make sure that ozone were removed. Then the reaction mixture was transferred to a dropping funnel and added dropwise to 125 mL aqueous solution of 10% sodium sulfite at 85° C. After completion of the addition, the mixture was heated at 95° C. for 30 min. Then the reaction mixture was cooled to room temperature and extracted 3 times with iso-hexane (150 mL). The combined org. layers were dried ($MgSO_4$) and evaporated in vacuo. The residue was purified by distillation to give 3.8 g (44%) of pure methoxymelonal (1). Boiling point: 90-95° C./0.20 mbar.

1. $O_3$, 0° C.
2. aq. $Na_2SO_3$

2

1

Methoxymelonal

The invention claimed is:
1. A process of forming methoxymelonal comprising the steps of subjecting methoxy citronellene (2) to ozonolysis, followed by a reductive work-up to give methoxymelonal, and the synthesis is set out in the scheme below:

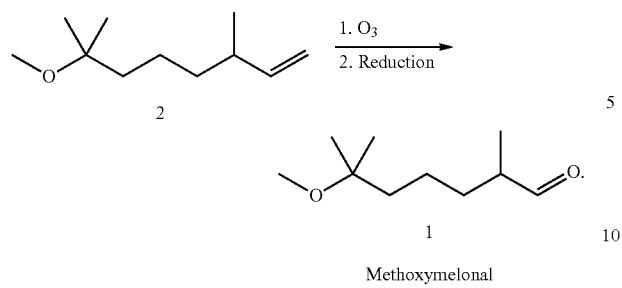

Methoxymelonal

2. The process according to claim 1 wherein the ozonolysis is carried out in a solvent selected from methanol or water.

3. The process according to claim 1 wherein the reductive work-up step is a hydrogenation carried out using palladium as a catalyst.

4. The process according to claim 1 wherein the reduction step is carried out using sulfites as reducing agents.

* * * * *